United States Patent
Qazi et al.

(10) Patent No.: US 6,242,243 B1
(45) Date of Patent: *Jun. 5, 2001

(54) TRICHOSPORON SP RRLY-15 (DSM 11829) AND ITS USE TO PREPARE S(+)-6-METHOXY-METHYL-2-NAPHTHALENE ACETIC ACID

(75) Inventors: Ghulam Nabi Qazi; Rajinder Parshad; Surrinder Koul; Subhash Chandra Taneja; Kanaya Lal Dhar; Ravi Ji Kotru; Sukhdev Swami Handa, all of Jammu (IN)

(73) Assignee: Council of Scientific & Industrial Research, New Delhi (IN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/050,011

(22) Filed: Mar. 30, 1998

(51) Int. Cl.[7] .................................................. C12N 1/18
(52) U.S. Cl. ........................ 435/254.1; 435/911; 435/136; 435/280
(58) Field of Search ...................................... 435/280, 136, 435/911, 254.1

(56) References Cited

U.S. PATENT DOCUMENTS 4,762,793 * 8/1988 Cesti ...................................... 435/280
5,516,690 * 5/1996 Evans ..................................... 435/280

* cited by examiner

*Primary Examiner*—Irene Marx
(74) *Attorney, Agent, or Firm*—Nath & Associates; Harold L. Novick

(57) ABSTRACT

This invention discloses a process for the use of a novel organism belonging to the genus Trichosporon sp. as whole wet or dry cell culture or cell free extract or crude enzyme or pure isolated enzyme The strain of Trichosporon sp. used in the process is designated as RRLY-15 and has been deposited in Deutsche Sammlung von Mikroorganismen und Zellkulturen GmbH (DSMZ). The invention also discloses the preparation of S(+)-6-methoxy-2-naphthalene acetic acid (naproxen) of formula (2) through enantioselective hydrolysis of a racemic mixture of alkyl esters of (±)-6-methoxy-α-methyl-2-naphthalene acetic acid of formula (1) where R represents —$CH_3$,—$C_2H_5$,—$C_3H_7$,—$C_4H_9$ and the like and S(+)- Naproxen is a medicinally important non steroidal anti-inflammatory drug.

24 Claims, 1 Drawing Sheet

Council of Scientific and Industrial Research
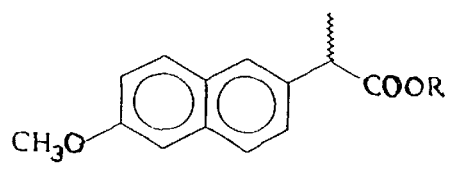
(1)
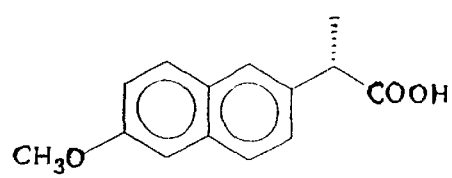
(2)
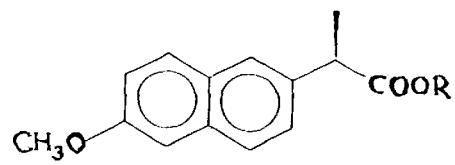
(3)
R = -CH₃, -C₂H₅, -C₃H₇, -C₄H₉.

TRICHOSPORON SP RRLY-15 (DSM 11829) AND ITS USE TO PREPARE S(+)-6-METHOXY-METHYL-2-NAPHTHALENE ACETIC ACID

FIELD OF INVENTION

This invention relates to the filed of biotechnology. It describes an efficient bio-resolution process for the preparation of an anti-inflammatory drug S(+)-6-methoxy-α-methyl-2-naphthalene acetic acid (naproxen) of formula (2). Through the bio-resolution process, two enantiomers of (±)-6-methoxy-a-methyl-2-naphthalene acetic acid alkyl esters are resolved. The bio-resolution is effected by the mediation of an organism belonging to the genus Trichosporon sp. The organism may be used in the form of whole wet cell pellet or dry cell powder or cell free extract or pure enzyme isolated from the cell culture. The use of Trichosporon sp. (RRLY-15) DSM 11829 is novel for kinetic resolution of the said compound through its maximum enantioselectivity and near theoritical yields.

PRIOR ART AND BACKGROUND OF THE INVENTION

S(+)-6-methoxy-α-methyl-2-naphthalene acetic acid of formula (2) belongs to the class of α-methyl aryl acetic acids also known as 2-aryl propanoic acids which in turn belong to an important class of non-steroidal anti-inflammatory drugs (NSAID). Most commonly used drugs in this class besides naproxen include ibuprofen, ketoprofen and fluriprofen. These drugs have wide applications in checking pain and inflammation caused by arthritis and related connective tissue diseases (Shen, T. Y.; Angew, Chem, Int.Ed., 1972, 11, 460). These drug molecules being chiral in nature appear as racemates, when synthesised through a normal chemical synthetic process. In recent years, the use of enantiomerically pure drugs in chemotherapy is becoming almost mandatory and FDA's of many countries are bringing in new drug legislations for this purpose. The use of enantiomerically pure drugs, not only improves the specificity of action, but also minimises the toxicity and undesirable load on the host. The validity of this statement is very true for α-aryl propanoic acid also. In case of (±)-6-methoxy-α-methyl-2-naphthalene acetic acid, the S(+) enantiomer is 28 times more active than its R(−) enantiomer (Roszokwski, A. P., Rooks, W. H., Tomolonis, A. J. and Miller, L. M. J. Pharmcol Exp. Ther, 1971, 179, 114). Another drug belonging to the same class of non-steroidal anti-inflammatory drug (NSAID) which till recently was being prescribed as a racemic mixture is ibuprofen. It has been observed that although the inactive R(−)-antipode of this drug is converted to S(+)-enantiomer in vivo via a CoA thioester intermediate, the epimerisation process leads to metabolic complications as R(−)-ibuprofen-CoA complex competitively inhibits many CoA dependent reactions, which results in perturbation of hepatocyte intermediary metabolism and mitochondrial function. Pure S(+)-ibuprofen may therefore be a preferred drug of future (Ann. Rep. Med. Chem. Vol 30(1995) p.298, Ed. James a Bristol, Academic Press inc. California).

As the chemical synthesis of compound (2) leads to the formation of racemic mixture, one or the other resolution techniques are employed for the separation of S(+) enantiomer (Harrison, I. T., Lewis, B., Nelson, P., Rooks, W., Roszwkoski, A., Tomolonis, A. J. and Fried, J. H. J. Med. Chem., 1970 13 203). These methods generally employ the selective crystallisation of dl-stereoisomeric salts by the use of expensive optically active amines such as cinconidine, dehydroabietyl amine acetate, phenyl ethyl amine etc. (Newman, P. in Optical Resolution Process for Organic Compound Vol.2(II) p.653 (1981), Manhattan College, New York). Resolution of (2) has also been carried out using camphor-10-sulfonic acid (Tsuchihashi, G., Tetrahedron Lett, 1982, 23, 5427).

Asymmetric synthesis of α-aryl propanoic acids offers another important methodology for obtaining enantiomerically pure compounds. Various strategies employed in these methods include Lewis acid catalyzed 1,2-aryl-migration, use of chiral catalysts in stereoselective C—C bond formation, hydroformylation, asymmetric hydrogenation etc. Asymmetric synthesis of α-aryl propanoic acids has recently been reviewed [Sonawane, H. R., Bellur, N. S., Ahuja, J. K. and Kulkarni, D. G., Tetrahedron Asym. 1992, 3(2), 162; Vill. C., Giordans, M., Pannosion, S. Sheldrak, G. N. in Naproxen: Industrial Asymmetric syn. (1992). p.303 Ed. Collins, A. N. and Crosby, J. N., Chechester, U.K.: Jia, C., Le, J., Zhonogguo Yiyao Zazhi 1990, 21(3) 137].

A number of reports related to the bio-resolution of (±)-naproxen have appeared in last ten years using hydrolases, lipases, esterases or proteases from bacterial, fungal or animal sources. A brief review is presented in the following lines.

*Candida cylinderacea* lipase was successfully used for the separation of S(±)-6-methoxy-α-methyl-2-naphthalene acetic acid through its chloromethyl ester (Gu, Qui-Ming; Chen, C. and Sih, C. J., Tetrahedron Lett. 1986, 27 (16), (1763). This work has also been patented (Sih, C. J., Eur. Pat. Appl. E.P. 227, 078, 01 Jul., 1987, U.S. Appl. 811, 260, 20$^{th}$ Dec., 1985). Some other important publications in resolution methods for (±)-naproxen and related α-methyl aryl acetic acids derivatives include (Quax, W. J, Broekhuizen, C. P., Applied Microbial. Biotechnol. 1994, 41 (4), 425; Smeets, J. W. H., Kieboom, A. P. G., Recl. Trav. Chim. Pays-Bass 1992, 111(11), 490, CA, 118: 212077; Mutasaers, J. H., G. M., Kooreman, H. J., Recl. Trav. Chim. Pays-Bas 1991, 110(05) 185, CA, 115-207622t; Gu, Q.; Zhongguo Gongyu Zazhi, 1991, 22(21) 49, CA, 115: 88688; Alkumark, S., Anderson, S., Chirality 1992, 4(1) 24, Wu, S. H., Guo, Z. W., Sih, C. J., J. Am. Chem. Soc. 1990, 112(5), 1990) Enantioselective esterification of racemic naproxen has also been carried out using Candida lipase in organic solvents] Shan-Wei, T., Hwa-Jou, W., Biocat., 1994, 11(1), 33 and J. Chem. Technol. Biotechnol., 1996, 65(3), 156].

A few other processes have been patented in the past for the kinetic resolution of (±)naproxen using different enzymes. For example the alkyl esters of (±)-naproxen were claimed to be resolved by the use of enzymes from Pseudomonas, Brevibacterium or Mycoplana species (Watanabe, I., Hosoi, A, Kobayashe, E., J.P., 6363396, 19 Mar., 1988, CA, 109:72056). Gist Brocades, employed *Bacillus thai* and other micro-organisms to hydrolyse alkyl esters of (±)naproxen (Gist Brocades, N.V., JP 63, 45,234 26 Feb., 1988, FR. Appl. 88.245 7 Jan, 1986, CA, 109: 168975). Resolution of esters of naproxen stereoisomers was achieved in a multiphase extractive membrane bioreactors in presence of *Candida cyclinderacea;* optically active naproxen was collected in aqueous phase (Matson, S. L. PCT Int. Appl. WO, 88,07,582 06 Oct., 1988 US Appl. 33, 962, 01 Apr., 1987: CA, 111; 113732). A process for the continuous manufacture of S(+)-naproxen was disclosed by Bianchi et al using corresponding alkyl, phenyl, tetrahydropyranyl or tetrahydrofuranyl esters catalyzed by immobilised *Candida cylinderacea* lipase. They obtained 1757 g of S(+) naproxen from 9387 g of (±)ester after 1200h of continuous operation of the reaction (Bianchi, D., Cesti, P., Pina, C., Battislet, E, Eur. Pat. Appl. E.P. 330, 217, 30 Aug., 1989, IT, 88/19, 532, 25 Feb., 1988, CA 112: 215, 202). Water soluble esters of (±) naproxen were hydrolyzed to produce chiral aryl propinoic acids in a two stage extractive membrane reactor (Matson, S. L., Wald, S. A., Zepp, C. M., and Dodds, D. R. PCT Int. Appl. WO 89,09,765, 19 Oct., 1989, US Appl. 178 735, 07 Apr., 1988, CA, 113: 171683). Hydrolytic resolution of (±)-α-methyl naphthylacetonitrile derivatives was achieved by Cornynebacterium nitrophilus in 98% ee (Yamamoto, K., Otsubo, K., Oishi, K., Eur. Pat. Appl. E.P. 348, 901, 03 Jan., 1990, JP Appl. 88/156, 911, 27 Jun., 1988, CA 113: 76605). In another approach for the production of S(+)-naproxen a filamentous fungi Cordyceps milioris was employed for isomerisation of R(−)-naproxen to S(+) naproxen (Reid, A. J., Phillips, G. T., Marix, A. F. and De Smet, M. J., Eur. Pat. Appl. E.P. 338, 645,25 Oct., 1989 GB Appl. 88/9, 434,21 April, 1988 CA, 113: 38895). Vinyl, ethyl, methyl esters of (±) naproxen were kinetically resolved using various hydrolases, lipases, esterases etc.; where vinyl ester was claimed to yield maximum resolution (Flling, G., Schlingmann, M., Reinhold, K., Ger, Offen, DE., 3, 919029, 13 Dec., 1990, Appl. 10 Jun., 1989. CA, 114; 245930). Liver enzyme from animals such as rabbit, horse, sheep etc. were also used. (Goswami, A., PCT Int. Appl. WO, 9113163; 05 Sep., 1991, US Appl. 484, 362, 21 Feb., 1990, CA, 115: 254315). Novel Exophiala withansia species was identified to be capable of resolving a-substituted propanoic acid into optically active enantiomers; S(+) naproxen was obtained in 92% ee (De Smet, Jose. M., Eur. Pat. Appl. E.P. 386, 848., 12 Sep., 1990, US Appl. 308, 591, 10 Feb., 1989, CA, 115: 7022). MIS. Syntex Pharmaceuticals Co. patented an ester hydrolase gene from Pseudomonas fluorescens cloned in E. coli for the enantioselective hydrolysis of racemic alkyl esters of naproxen (Chan, H. W., Salazar, F. H., EP 414, 247,27 Feb. 1991, US Appl. 398, 102, 24 Aug. 1989, CA, 115, 236 99). Water soluble ethyl sulphate of (+) naproxen was converted into R(−) naproxen using Prozyme 6 (Serine protease of Aspergillus onyzae) in 79.8% yields (Dodds D. R. Zepp, C. M., Rossi, R. F. Eur. Pat. Appl. E.P. 461, 043, 11 Dec. 1991, US appl. 535, 303, 08 June, 1990, CA. 116: 150171). Microbes from Brevibacterium, Bacteridium, Micrococcus, Bacillus etc. were cultivated and used for the resolution of α-aryl propanoic esters in high ee (Battistel, E., Bianchi, D., Cesti, P., Franzosi, G., Tassinori, R., Spezia, S. Eur. Pat. Appl. E.P. 510, 712, 28 Oct., 1992 15 Apr., 1991/M, 1154. 26 Mar., 1991, CA, 118: 58236). Similarly amides and nitrites were hydrolysed enzymatically to corresponding acids for the manufacture of optically pure naproxen (Ootsubo, K., Yamamoto, K., J.P. 0576, 390, 30 Mar., 1993, Appl. 91/228, 560, 15 Aug., 1991, CA, 119: 93701 and Fallow, R. D. Steiglitz, B., PCT Int. Appl. WO 94, 06, 930, 31 Mar., 1994, US Appl. 948, 185, 21 Sept., 1992, CA, 121: 81125). (±)-Naproxen methyl ester was converted in 35% yields to S(+) naproxen using a panel of micro-organisms most suitable being Zoffeillor latipes (Chan, H. W., Freeman, R., Salazar, H., Beck, S. R., Synder, R. C., Cain, R. O., Roberts, C. R., Felix, H., Phelps, P., Heefner, D. L., PCT Int. Appl. WO 93,23,547, 25 Mar., 1993, US Appl. 883,658, 15 May, 1992, CA, 120: 189868). An enzyme from an organism of the genus Ceracystis was identified and its gene when cloned and expressed in E. coli was used for the production of R(−) naproxen in >95% ee and 26% yields (Julie, W., Hazel, B., Anthony, W. R., PCT Int. Appl. WO 9420, 634, 15 Sep., 1994, GB. Appl. 93/4351, 03 Mar., 1993 CA; 122: 8143).

The number of reviews and patents appearing in the last few years for the preparation of optically pure naproxen from the racemic mixture and over the counter (OTC) status of this drug in USA underline the importance of S(±) naproxen and related compounds as an anti-inflammatory drug of choice. Therefore, production of S(±) naproxen from the racemic mixture enzymatically or by other methods both chemical or catalytic has remained on the top of the priorities for many R&D institutions and pharmaceutical companies world over. The major producers of naproxen till date employ routes involving classical resolution of racemates via diastereoisomeric salt crystallisation.

However, for the last ten years more efforts have been directed towards the development of bio-resolution methods. Biological/enzymatic methods of resolution have the advantage over chemical or other conventional methods for being simple, catalytic, relatively economical and environment friendly. Since enzymes are highly stereo-selective and substrate specific, it therefore requires a specific enzyme for specific bio-conversion. The enzymes available commercially for biotransformation may not display the required selectivity and specificity for the desired bio-conversion and may be of academic interest only. Therefore, the identification, selection and generation of a suitable enzyme is an essential requirement for bio-transformations.

DETAILED DESCRIPTION OF THE INVENTION AND PREFERRED EMBODIMENT

The yeast RRLY-15 used in this process has been isolated by the applicants from local fermented cheese "Kalari" as per the procedure described by the Beech and Davenport, Methods in Microbiology (ed.) Booth, C.Vol. 14, p.153, 1971, Academic press N.Y. The source of the organisms, the local cheese samples, were shredded and incubated at 25° C. for 2 days in a medium containing yeast extract 0.025% (W/V) and Olive oil 0.5% (V/V). The resultant culture was further screened for lipase/esterase producing colonies isolated on a selective medium comparising of MYPG (maltose, yeast, estract, peptone, glucose) agar containing 0.1 to 0.2% (w/v) triglycerol such as triacetin and 0.005% bromocresol green as an indicator. The colonies of Yeasts causing clearing zones due to hydrolysis of triglycerol and yellow colouration zone due to organic and liberation were regarded as putative lipase/esterase producers. The selected colonies were further screened for lipase/esterase production by enzyme assay in which a known quantity of fresh whole cell pellet was incubated in 0.05 M Tris buffer containing 200 μmol triacetin and the rate of hydrolysis was monitored by titration with 10 mmol sodium hydroxide solution. Stereoselectivity of the primarily selected isolated was assayed on the basis of selective hydrolysis of methyl phenyl carbinol. Several such colonies that indicted stereoselectivity as depicted by chiral high pressure liquid chromatography (HPLC) analysis were subjected to assay for ester hydrolysis of alkyl esters of S(±)6-methoxy-α-methyl-2-naphthalene acetic acid. One such colony that depicted maximum hydrolase activity out of several hundreds of colonies was used for further process development. The organism was identified according to Lodder, J. (ed.), The Yeast—A taxonomic study $2^{nd}$ edn. 1970, Amsterdam: North Holland. It was classified as an imperfect Yeast belonging to family Cryptococcaceae sub-family Trichosporoidea. The isolated strain was further identified as belonging to the genus Trichosporon because of its characteristics formation of loose budding cells and true mycelium falling apart into arthospores/blastospores thus distinguishing the genus from Candida. It is also distinct from genus Geotricum which lacks the formation of blastospores. Another distinguishing characteristics of the two genera namely Geotricum and Trichosporon, is the formation of aerial, septate hyphae which disintegrate into dry conidia in the former whereas the latter has mucoid, slimy colonies and lack aerial hyphe. The isolated organism in the present invention was identified as Trichosporon also because of its blastoconidia being enteroblastic, a typical characteristic of the genus.

The yeast strain designated by us as RRLY-15 is maintained at the culture collection unit of the Regional Research Laboratory (CSIR), Jammu, a constitutent Laboratory of the applicants and has also been deposited at Deutsche Sammlung von Mikroorganismen and Zellkulturen GmbH (DSMZ) Braunchweig, Germany under their Accession No.DSM 11829.

The yeast strain may be maintained on solid medium containing peptone, yeast extract, malt extract, glucose and agar.

In the yeast cell propagation and enzyme production process the carbon source used is a carbohydrate like glucose, fructose, sucrose, lactose etc. or a raw source containing these carbohydrates. The organic nitrogen source used is yeast extract, malt extract, corn steep liquor, peptone etc. The inorganic nitrogen source may be ammonia, ammonium nitrate, ammonium sulphate, urea etc. The culture may be prepared under aerobic conditions in shaken flasks or in stirred vessels wherein culture broth may be adequately circulated or mechanically agitated at a rate in the range of 200–700 revolutions per minute (rpm), especially at a rate in the range of 200–500 rpm. The culture broth may be aerated at a rate in the range of 0–2 volumes per volume (vvm), especially at a rate in the range 0.1–1.2 vvm.

The cell propagation process may be based on batch or fed batch or continuous fermentation procedure. The optimum cell density and the enzyme activity may be obtained in $15 \geq 24$ h in a batch process. The cells may be harvested from the culture broth by ultrafiltration/centrifugation. The harvested cells may be either used as such or dried in a lyophiliser or homogenized/ultrasonicated and the resultant cell free extract lyophilised to dry powder. The wet cell pellet (20–25% dry solid) may show the ester hydrolase activity of 15–20 KU/g (one unit of enzyme is that amount of wet cell pellet which hydrolyses 1 $\mu$mol of triacetin in 1 min. and KU means 1000 units). Alternatively, the wet cell pellet may be subjected to high shear by ultrasonification, homogenisation with or without abrasive materials and the cell free extract obtained after removal of cell debris used as the source of the enzyme either directly or crude enzyme may be isolated by fractional precipitation with such precipitating agents like acetone, ethyl alcohol, polypropylene glycol ammonium sulphate etc. and the resultant powder used as the enzyme. Yet alternatively the desired enzyme may be isolated from the crude protein as per the standard enzyme purification procedures used in the state of art which may comprise series of steps like ammonium sulphate precipitation, gel filtration, ion exchange and affinity chromatography on sephadex, DEAE sephadex and phenyl agarose obtaining pure protein with lipaselesterase activity of 1500–1700 KU/g and molecular weight of the pure enzyme relative to standard proteins of known molecular weight was found to be 40 to 50 kilo Daltans.

The production of an esterase/lipase from the strain RRLY-15 (DSM 11829) is an important function of this strain and the enzyme is unique for its substrate specificity and stereo selectivity. The strain as well as the stereo selective hydrolase isolated from it was found to depict stable biochemical characteristics at 30–35° C. at pH value of 6–9 for 4–5 days. The isolated enzyme in its lyophilized state in crude or pure form did not lose its biochemical characteristics when stored at 4° C. for a year. The yeast strain RRLY-15 (DSM 11829) or its isolated enzyme in crude or pure form may either be used for single reaction or separated from the reaction mixture after the completion of the reaction by appropriate means such as ultrafiltration and reused for kinetic resolution reaction in water or in buffers or in organic solvents. The yeast strain RRLY-15 (DSM 11829) as such or its cell free extract or the crude or pure enzyme isolated from it was found to be highly enantioselective, therefore, useful for kinetic resolution of racemic mixtures, especially that of alkyl esters of S(+)-6-methoxy-α-methyl-2-naphthalene acetic acid (Naproxen) of formula (1). In our endeavour to prepare the compound of formula (2) we have used the biomass of Trichosporon sp. RRLY-15, its cell free extract, crude and/or pure enzyme derived from it and effectively resolved the corresponding alkyl esters of formula (1) into S(+)-6-methoxy-α-methyl-2-naphthalene acetic acid of the formula (2).

The kinetic resolution or the preferential hydrolysis of only one of the two enantiomeric esters in the present case may be due to extremely large difference in the rate of hydrolysis of the two enantiomers comprising the racemic mixture by the cell culture or cell free extract or crude or pure enzyme isolated from the organism belonging to genus Trichosporon designated as RRLY-15 (DSM 11829). A racemate or racemic mixture is an equimolar mixture of the enantiomeric species and such mixture is devoid of any optical activity. In the chemical formula it may be represented by a prefix (±), (dl), or (RS) or rac- and the individual isomer or enantiomer which is represented by a prefix (d) or (1); or (+) or (−); where as (R) or (S) represents absolute configuration.

The resolved S(+)-6-methoxy-α-methyl-2-naphthalene acetic acid (naproxen) of formula (2) has following specifications:

White crystalline solid crystallised from methanol m.p. 157° C. analyzed for $C_{14}H_{14}O_3$ (M+ at m/e 230) $[\alpha]_D^{25}$+67° (CHCl$_3$. Cl.0).

The use of Tricosporon species RRLY-15 (DSM 11829) in the invention for the purpose of kinetic resolution is novel as is evident from the literature scan. The strain is highly specific for the enantioselective hydrolysis of racemic ester of 6-methoxy-α-methyl naphthalene acetic acid of formula (1). The catalytic properties for the kinetic resolution remain the same as and when Tricosporon species RRLY-15 is used as whole wet cell mass or lyophilised cell mass or the cell free extract or crude enzyme or the pure isolated is used in an aqueous or buffer solution. The most significant point of distinction of the present process is that selectivity of 99:1 for S(+) and R(−) esters respectively is obtained even when substrate concentration upto 160 g/l (>650 mmol) is used.

Therefore, the main objective of the present invention is to provide an efficient and economical bio-process for the preparation of S(+)-6-methoxy-α-methyl naphthalene acetic acid of formula (2) in a single operation using whole wet or dry microbial cell or cell free extract or the crude enzyme or pure enzyme isolated from Trichosporon Sp. RRLY-15 (DSM 11829).

The kinetic resolution is effected by enantioselective hydrolysis of the corresponding S(±)-alkyl esters, such as methyl, ethyl, butyl and the like of formula (1) to produce enantiopure and required isomer (eutomer) S(+)-6-methoxy-α-methyl naphthalene acetic acid or (naproxen) of formula (2) in yields upto 47% (94% theoretical) and enantiomeric excess (ee 7 98%).

Another objective is to directly produce pure S(+)-sodium naproxenate (another desirable form of the drug) from racemic mixture of (±)-6-methoxy-α-methyl naphthalene acetic acid and alkyl esters, such as methyl ethyl, butyl and like of formula (1).

Yet another objective is to separate and produce alkyl ester of R(−)-(6)-methoxy-α-methyl naphthalene acetic acid of formula (3) by kinetic resolution of (±)-6-methoxy-α-methyl naphthalene acetic acid alkyl esters, such as methyl, ethyl, butyl and like of formula (1).

Still another objective of the invention is to produce enriched alkyl esters of R(−)-6-methoxy-α-methyl naphthalene acetic acid of formula (3) which may be reused after recemisation.

Accordingly, the present invention discloses the use of Trichosporon sp. RRLY-15 (DSM 11829) as whole cells in wet or dry form or cell free extract or the crude or the pure isolated enzyme for the production of S(+)-naproxen of formula (2) through selective hydrolysis of the alkyl esters of the formula (1). The process comprises of following steps after the propagation of Trichosporon sp. RRLY- 5 by fermentation techniques as per the above described state of the art.

(a) Treating (±)-6-methoxy-α-methyl naphthalene acetic acid alkyl esters, such as methyl, ethyl, butyl and the like of formula (1) at a concentration 0.1M to 0.7M with whole yeast, cell culture of Trichosporon sp. RRLY-15 (DSM 11829) or the disrupted cell powder obtained after lyophilisation or the enzyme isolated there from as the cell free extract or the crude or pure enzyme as lyophilized powder in water or buffer solution.

(b) Effecting the kinetic resolution at a temperature in the range of 5–45° C. and pH range of 4–10.

(c) Separating S(+)-6-methoxy-α-methyl naphthalene acetic acid of formula (2) and alkyl ester of R(−)-6-methoxy-α-methyl naphthalene acetic acid of formula (3) by conventional methods. The separation may be effected by solvent extraction of the acidified reaction mixture comprising cell mass/enzyme, resolved S(+)-acid of formula (2) and enriched R(−)-ester of formula (3) using toluene, dichloromethane, ethyl acetate, butyl acetate and the like followed by partitioning between organic solvent layer comprising of ester of formula (3) and aqueous basic layer comprising of alkali salt of S(+) acid of formula (2). The salt formation can be effected using an alkali solution such as sodium hydroxide, potassium hydroxide, sodium carbonate or the like. The S(+)-naproxen is then precipitated by acidification followed by filtration or by solvent extraction.

(d) Alternatively the S(+)-naproxen may be directly obtained from the reaction mixture as its alkali salt during the above process by ultrafiltration/centrifugation.

The invention is described in detail in examples given below which are given by way of illustration only and, therefore, these examples should not be construed as to restrict the scope of the reaction.

EXAMPLE 1

Preparation of (+)-6-methoxy-α-methyl-2-naphthalene acetic acid of formula (2) by kinetic resolution of (±)-6-methoxy-α-methyl-2-naphthalene acetic acid methyl ester of formula (1) using wet whole cell culture of Trichosporon sp. RRLY-15 (DSM 11829).

(i) Culture medium, comprising of 1.5% of glucose, 0.05% potassium dihydrogen phosphaste ($KH_2PO_4$) 1.0% corn steep liquor, and 0.3% of urea, pH 6.8 before sterilization and 6.5 after sterilization was prepared and dispensed in shake flasks (200 ml each) and in a 10.1 Stainless Steel (SS 304s) fermenter (working volume 7.5.1) and autoclaved. The preculture of the strain Trichosporon sp. RRLY-15 (DSM 11829) was prepared in the shake flask by inoculating a loopful of the culture prepared on solid agar medium and shaker incubating the flask at 30° C. The 24 hold pre-culture thus produced was inoculated into the culture medium and fermentation carried out at 500 rpm, 0.5 vvm aeration rate and constant temperature for 28° C. for 15–18 hours. The culture was thereafter centrifuged to collect the yeast cells. The cell pellet was washed twice with water and used for kinetic resolution studies directly.

(ii) 122 g (500 mM) of racemic methyl ester of 6-methoxy-α-methyl naphthalene acetic acid of formula (1) was added to 1000 ml water containing 300–350 g of above wet cell mass of Trichosporon sp. RRLY-15 (DSM 11829). The reaction mixture was stirred for 48 hrs. at 30° C. during which the pH of the solution was maintained at 8±1 through external addition of 1M sodium hydroxide solution. Thereafter the contents of the reaction mixture were acidified to pH 2–3 with 10% v/v sulphuric acid and total solids separated by centrifugation/filtration. The dried solid mass comprising of cell mass, S(+)-Naproxen and enriched R(−)-Naproxen ester was extracted with ethylacetate (500 ml). The free S(+)-Naproxen acid was separated from organic solvent by extraction with 10% w/v sodium hydroxide. The organic layer was washed with water and dried over anhydrous sodium sulphate. Stripping off of the organic solvent furnished 66.5 g (270 mM,) enriched R(−)-6-methoxy-α-methyl-2-naphthalene acetic acid methyl ester of formula (3). The basified aqueous layer containing S(+)-sodium naproxen was acidified with dilute acid solution (10% v/v) and white precipitate filtered, washed with water and dried to obtain (47.50 g, 210 mM) pure S(+)-6-methoxy-α-methyl-2-naphthalene acetic acid of formula (2), m.p. 157° C., ee>98% (chiral HPLC). The ester hydrolysis yield corresponded to the 46.47% equivalent to 93% theoretical conversion.

EXAMPLE 2

Preparation of sodium S(+)6-methoxy-α-methyl-2-naphthalene acetic acid of formula (2) by kinetic resolution of (+) 6-methoxy-α-methyl-2-naphthalene acetic acid methyl ester of formula (1) using dried whole cell culture of Trichosporon sp. RRLY-15 (DSM 11829).

(i) The yeast cell mass (300 g) Trichosporon sp. RRLY-15 (DSM 11829) prepared as described in example 1 was lyophilised at 0° C. to obtain 90 g dried whole cell culture. The lyophilised yeast powder was used directly for the kinetic resolution catalysis.

(ii) 61 g (250 mM) of racemic methyl ester of 6-methoxy-α-methyl naphthalene acetic acid of formula (1) was added to 500 ml of water containing 50–60 g dry cell mass of Trichosporon sp. RRLY-15. The reaction mixture was stirred at 800 rpm for 45 hrs. at 30° C. during which the pH of the solution is maintained at 7.0±0.1 through external addition of 1M sodium hydroxide solution. During the reaction the sodium salt S(+)-naproxen formed was continuously removed by centrifugation/ultrafilteration as aqueous solution and the reaction mixture replenished with water to maintain the volume of the reaction mixture. This operation was repeated four times during the reaction period to remove most of the sodium salt of S(+)-naproxen. The reaction mixture thereafter, was acidified to pH 2–3 with 10% v/v sulphuric acid and the total solids were separated by centrifugation/filtration. The wet solid mass comprising cell mass, some S(+)-Naproxen and enriched R(−)-Naproxen ester was extracted with toluene (500 ml). The free S(+)-Naproxen acid was separated from organic solvent by extraction with calculated amount of 10% w/v sodium hydroxide. Organic layer was washed with water and dried over anhydrous sodium sulphate. Stripping off the organic solvent furnished 33.25 g (136 mM) enriched R(−)-6-methoxy-α-methyl-2-naphthalene acetic acid methyl ester of formula (3). The combined aqueous layer comprising of S(+)-sodium naproxen was dried under vacuum to yield (25.3 g, 105 mM), white powder of sodium S(+)-6-methoxy-α-methyl-2-naphthalene acetic acid of the formula (2), ee>98% (chiral HPLC). The yield corresponded to 46.5% hydrolysis (93% of theoretical).

EXAMPLE 3

Preparation of S(+)-6-methoxy-α-methyl-2-naphthalene acetic acid of formula (2) by kinetic resolution of (±) 6-methoxy-α-methyl-2-naphthalene acetic acid ethyl ester of formula (1) using wet whole cell culture of Trichosporon sp. RRLY-15 (DSM 11829).

(i) The yeast cell mass Trichosporon sp. RRLY-15 (DSM 11829) prepared as in example 1 was used for the kinetic resolution catalysis.

(ii) To a suspension of 50 g (194 mM) of racemic ethyl ester of 6-methoxy-α-methylnaphthalene acetic acid of formula (1) in 400 ml of phosphate buffer (0.1M) at pH 18 was added 150–160g (22% solid) of wet cell mass of Trichosporon sp. RRLY-15 (DSM 11829). The reaction mixture was stirred at 800 rpm for 50 hrs at 37° C. and pH of the solution maintained at 7–8 by adding 1M sodium hydroxide solution externally in a pH stat. The pure S(+)-naproxen was separated from the reaction mixture by the method described in example 1 yielding enriched R(−)6-methoxy-α-methyl-2-naphthalene acetic acid ethyl ester of formula (1) 28 g and S(+)6-methoxy-α-methyl-2-naphthalene acetic acid of formula (2) 20.12 g, 84 mM ee=98% (chiral HPLC).

EXAMPLE 4

Preparation of S (+) 6-methoxy-α-methyl-2-naphthalene acetic acid of formula (2) by kinetic resolution of (+) 6-methoxy-α-methyl-2-naphthalene acetic acid methyl ester of formula (1) using cell free extract (crude) enzyme isolated from the cells of Trichosporon sp. RRLY-15 (DSM 11829).

(i) 400g cell mass of Trichosporon sp. RRLY-15 (DSM 11829) was prepared as described in example 1, suspended in 500 ml water and to it 1000 ml glass beads 500 μm size, the mixture was vortexed for 15 min. at 0–4°. The vortexed mix was centrifuged to obtain 350 ml of cell free extract. The process was repeated thrice to obtain 1050 ml of cell free extract. The cell free extract was used for the kinetic resolution catalysis.

(ii) A suspension comprising 122 g (500 mM) racemic methyl ester of 6-methoxy-α-methyl naphthalene acetic acid of formula (1) in 1000 ml aqueous protein solution bearing 7500 KU of crude lipase isolated from Trichosporon sp. RRLY-15 (DSM 11829) as described above was stirred for 40 hours at 30° C. during which the pH of the solution was maintained at 8±1 through the external addition of 1M sodium hydroxide solution. Thereafter, the reaction mixture was centrifuged/ultrafiltered to separate the soluble portion comprising S(+)-Naproxen acid as sodium salt and enzyme protein. The solids comprising mainly the enriched R(−)-6-methoxy-α-methyl-2-naphthalene acetic acid methyl ester was washed with 50 ml (100 mM) NaOH followed by water. The solids on drying furnished 66.3 g (271 mM) the enriched R(−)-6-methoxy-α-methyl-2-naphthalene acetic acid methyl ester of formula (3). The combined aqueous phase passed through a dialiser/ultrafilter to remove the enzyme protein. Filtered aqueous portion was acidified to pH 3.0 with 1M sulphuric acid and the precipitate of the free acid washed with water and dried to yield S (+) 6-methoxy-α-methyl-2-naphthalene acetic acid of formula (2). (52.50 g, 228 mM) ee>98% (chiral HPLC). Thus 46.5% ester hydrolyses corresponding to 93% theoretical conversion was obtained.

EXAMPLE 5

Preparation of S (+) 6-methoxy-α-methyl-2-naphthalene acetic acid of formula (2) by kinetic resolution of (+) 6-methoxy-α-methyl-2-naphthalene acetic acid methyl ester of formula (1) using pure enzyme isolated from the cells of Trichosporon sp. RRLY-15.

(i) Crude enzyme of yeast cell Trichosporon sp. RRLY-15 (DSM 11829) was prepared as given in example 4. The desired enzyme was isolated from the crude cell extract by purification process comprising ammonium sulphate precipitation followed by gel filtration, ion exchange and affinity chromatography on sephadex, DEAE sephadex and phenyl agarose. The purified enzyme preparation thus obtained was used for the kinetic resolution catalysis.

(ii) A suspension comprising of 122 g (500 mM) racemic methyl ester of 6-methoxy-α-methyl naphthalene acetic acid of formula (1) in 1000 ml aqueous protein solutions bearing 7000 KU of pure lipase enzyme isolated from Trichosporon sp. RRLY-15 (DSM 11829) was stirred for 40 hrs. at 30° C. during which the pH of the solution was maintained at 8±1 through external addition of 1M sodium hydroxide solution. Thereafter the reaction mixture was centrifuged/ultrafiltered to separate the soluble portion comprising S(+)-Naproxen acid as sodium salt and enzyme protein. The solids comprising mainly the enriched R(−)-6-methoxy-α-methyl-2-naphthalene acetic acid methyl ester was washed with 50 ml (100 mM) NaOh followed by water. The solids on drying furnished 66.4 g (272 mM) enriched R(−)-6-methoxy-α-methyl-2-naphthalene acetic acid methyl ester of formula (3). The combined aqueous phases passed through a dialyser/ultrafilter to remove the enzyme protein. Filtered aqueous portion was acidified to pH 3.0 with M sulphuric acid and the precipitate of the free acid washed with water and dried to yield S(+) 6-methoxy-α-methyl-2-naphthalene acetic acid of formula (2), (52.40 g), 227 mM) ee>98% (chiral HPLC). The yield corresponded to 46.3% ester hydrolysis (92.6% theoretical).

Reference to examples 4 and 5.

1. one unit of enzyme is that amount of enzyme which hydrolyses 1 μmol of triacetin in 1 minute of KU represents 1000 units.

References to the examples 1–5

HPLC conditions

Column: Lichro CART 250-4 (S, S)-Whelk-O 1, 5 μm

Mobile phase: n-hexane: 2-propanol: acetic acid (90:10:0.25)

Flow rate: 1.2 ml/min.

Detection: UV 254 nm

What is claimed is:

1. A biologically pure culture of Trichosporon sp., RRLY-15 (Regional Research Laboratory, Jammu, India) and also deposited in Deutsche Sammlung von Mikroorganismen and Zellekulturen GmbH (DSMZ) Braunschweig, Germany, under accession No. DSM 11829.

2. An efficient bio-process for the preparation of S(+)-6-methoxy-α methyl naphthalene acetic acid of Formula (2):

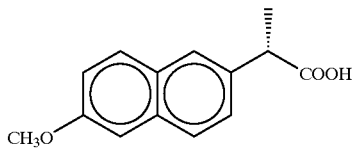

(2)

by enzymatic resolution of an (+)-6-methoxy-α-methyl naphthalene acetic acid alkyl ester of Formula (1):

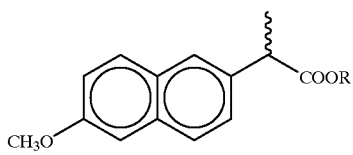

(1)

where R is —CH$_3$,—C$_2$H$_5$,—C$_3$H$_7$ or —C$_4$H$_9$ wherein a kinetic resolution process is effected with cells or an enzyme obtained from a strain of Trichosporon sp. RRLY-15, DSM 11829, so as to produce the desired compound of formula (2) in 90–93% theoretical yield and >98% enantiopurity at a substrate concentration of 60 to 160 g/l.

3. The process of claim 2 wherein the resolution is effected by cells of Trichosporon sp., RRLY-15, by the use of a whole wet cell mass or by the use of lyophilised cells or by the use of cell free extract.

4. The process of claim 2 wherein the separation of S(+)-6-methoxy-α methyl naphthalene acetic acid and its R(-)-ester is effected by solvent extraction or salt formation which is effected by using an alkali solution selected from the group consisting of NaOH and KOH followed by solvent extraction to remove alkyl ester of R(-)-6-methoxy-αmethyl naphthalene acetic acid, the S(+)-6-methoxy-αmethyl naphthalene acetic acid then being precipitated by acidification followed by filtration or solvent extraction.

5. The process of claim 2 wherein the S(+)-6-methoxy-α methyl naphthalene acetic acid by-product of the process is isolated as the sodium salt.

6. The process of claim 2 wherein the kinetic resolution is carried out in a buffer solution selected from the group consisting of phosphate borate and tris solutions.

7. The process of claim 2 wherein, the kinetic resolution is carried out in distilled water.

8. The process of claim 2 wherein the kinetic resolution is carried out in the pH range of 5–9.

9. The process of claim 2 wherein the kinetic resolution is effected at a temperature in the range of 20–40° C.

10. The process of claim 2 wherein selectivity for S(+) and R(-) ester is obtained in the ratio 99:1 even when substrate concentration used is 160 g/l.

11. The process of claim 2 wherein S(+)-6-methoxy-α methyl naphthalene acetic acid and R(-) ester is recovered after resolution by solvent extraction after acidification.

12. The process of claim 2 wherein a solvent used for extraction of S(+)-6-methoxy-α methyl naphthalene acetic acid is a chlorinated solvent.

13. The process of claim 2 wherein a solvent used for extraction of S(+)-6-methoxy-α methyl naphthalene acetic acid is selected from the group consisting of chloroform and dichloromethane.

14. The process of claim 2 wherein a solvent used for extraction of S(+)-6-methoxy-α methyl naphthalene acetic acid is a member selected from the group consisting of ethyl acetate, diethyl ether and diisopropyl ether.

15. The process of claim 2 wherein the separation of cells after biotransformation is effected by filtration or centrifugation.

16. The process of claim 2 wherein the mixture of the (-)-6-methoxy-α-methyl naphthalene acetic acid alkyl ester of Formula (1) and the strain of Trichosporon sp. RRLY-15 is acidified to pH 2–3 by the addition of 10% w/v sulphuric acid and S(+)-6-methoxy-α methyl naphthalene acetic acid is obtained as precipitate.

17. The process of claim 2 wherein the hydrolysed S(+)-6-methoxy-α methyl naphthalene acetic acid is recovered as its sodium salt directly by the use of NaOH in 10% w/v.

18. The process of claim 2 wherein an ester of Formula (3):

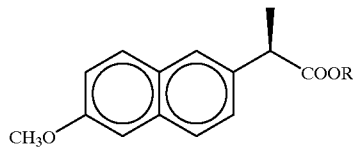

is recovered by solvent extraction or acidification of the aqueous solution to pH 2–4 and the acid of Formula (2):

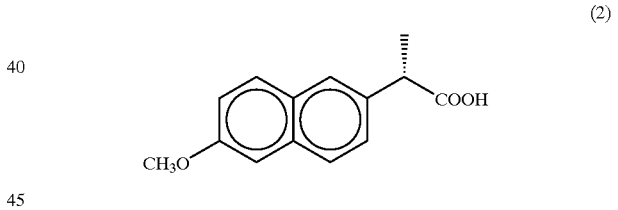

(2)

is recovered by filtration or solvent extraction, wherein R is —CH$_3$, —C$_2$H$_5$, —C$_3$H$_7$ or —C$_4$H$_9$.

19. The process of claim 2 wherein the resolution is effected by an enzyme from the strain of Trichosporon sp., RRLY-15.

20. The process of claim 19 wherein the enzyme is crude.

21. The process of claim 19 wherein the enzyme is pure.

22. The process of claim 19 wherein the enzyme is in solution.

23. The process of claim 22 wherein the solution is buffered.

24. The process of claim 23 wherein the solution is buffered by a buffering agent selected from the group consisting of phosphate, Tris and borate.

* * * * *